| United States Patent [19] | [11] Patent Number: 4,980,167 |
|---|---|
| Harashima et al. | [45] Date of Patent: Dec. 25, 1990 |

[54] SILICONE COSMETIC COMPOSITION

[75] Inventors: Asao Harashima, Ichihara; Keiji Yoshida, Nihonbashi, both of Japan

[73] Assignee: Dow Corning Toray Silicone Company, Ltd., Tokyo, Japan

[21] Appl. No.: 469,859

[22] Filed: Jan. 24, 1990

[30] Foreign Application Priority Data

Jan. 31, 1989 [JP] Japan .................................. 1-21947

[51] Int. Cl.$^5$ ..................... A61K 7/00; A61K 7/02; A61K 7/027
[52] U.S. Cl. ..................... 424/401; 424/63; 424/64; 424/69; 514/845; 514/847
[58] Field of Search ................. 424/401, 63, 64, 69, 424/65, 78; 252/DIG. 5; 514/844–848

[56] References Cited

U.S. PATENT DOCUMENTS

| 4,574,082 | 3/1986 | Tietjen et al. | 424/63 |
| 4,578,266 | 3/1986 | Tietjen | 424/63 |
| 4,837,011 | 6/1989 | Macchio et al. | 424/69 |
| 4,855,129 | 8/1989 | Steinbach et al. | 424/63 |
| 4,892,726 | 1/1990 | Yonekura et al. | 424/63 |
| 4,906,458 | 3/1990 | Shigeta et al. | 424/63 |

FOREIGN PATENT DOCUMENTS 61-171415 8/1986 Japan .
61-194009 8/1986 Japan .

*Primary Examiner*—Merrell C. Cashion, Jr.
*Assistant Examiner*—A. Hulina
*Attorney, Agent, or Firm*—Sharon K. Severance

[57] ABSTRACT

The cosmetic composition of the present invention exhibits excellent lubricancy since it contains silicone rubber powder containing 0.50–80 wt % of silicone oil. When it is coated on the skin, no foreign sensations or irritations are reported. A smooth and moist texture is obtained.

3 Claims, No Drawings

SILICONE COSMETIC COMPOSITION

The present invention concerns a cosmetic composition which comprises a silicone rubber powder whereby the silicone rubber powder contains a silicone oil. The cosmetic agents of the instant invention are less irritating to the skin and offer lubricancy to the cosmetic composition.

BACKGROUND OF THE INVENTION

Numerous attempts have been made to enhance the Properties of cosmetic agents by the addition of various Powders. For example, Japanese Patent Application Laid-Open No. 61-171415 teaches a skin detergent composition which contains 1-50 weight percent of a spherical or amorphous plastic powder with a particle size of 300 to 900 microns. The plastic powders taught in the '415 patent do not include silicones. Due to the hardness of the plastic, some discomfort or irritation to the skin may result when used. Additionally, the powders lack lubricancy which again may cause discomfort or irritation when applied to the skin.

Japanese Patent Application Laid-open No. 61194009 teaches makeup cosmetics containing a cured organopolysiloxane powder. The cured organopolysiloxane powders contained in the cosmetics taught in the '009 patent impart smooth coatability and a moist feel. However, they lack lubricancy thereby resulting in some irritation to the skin.

U.S. Patent Application Ser. No. 07/205,712, having the same assignee and inventors as the instant application, teaches a facial cleanser containing a cured organopoly-siloxane powder whereby the organopolysiloxanes impart some cleaning properties to the facial cleanser composition. Again, the organopolysiloxanes used in the facial cleansers lack lubricancy.

The foremost objective of the present invention is to provide a cosmetic composition which exhibits various excellent properties such as high lubricancy, absence of skin discomfort or irritation, smooth texture, and moist texture, by using a silicone rubber powder whereby the silicone rubber powder contains a silicone oil.

THE INVENTION

The present invention concerns a cosmetic composition which contains silicone powder whereby the silicone rubber powder contains 0.5–80 percent by weight of a silicone oil.

The silicone rubber powder used in the present invention constitutes the most notable characteristic of the present invention. The silicone rubber powder contributes to the smooth and moist texture of the cosmetic composition of the present invention. If the cosmetic composition of the present invention is used as a face-cleansing cosmetic composition, furthermore, the silicone powder removes organic pollutants. The aforementioned silicone rubber powder is usually spherical. The optimum average particle size of the silicone powder depends on the cosmetic composition. For example, when a makeup composition or antiperspirant composition is prepared, the average particle size should be 0.1–1,000 μm, preferably 0.1–100 μm. When a face-cleansing composition is prepared, the average particle size should be 1–3,000 μm, preferably 1–1,000 μm.

There are no special restrictions on the silicone oil which partially constitutes said silicone rubber powder as long as it is inert to the Silicone rubber. Generally speaking, however, silicone oils with a viscosity (at 25° C.) of 10–1,000 centistoke (cst.) are desirable. Examples of such silicone oils include, but are not limited to. dimethylpolysiloxane in which trimethylsiloxy groups are present at the terminal ends dimethylsiloxanemethylphenylsiloxane copolymer in which trimethylsiloxy groups are present at the terminal ends, dimethylsiloxanediphe nylsiloxane copolymer in which trimethylsiloxy groups are present at the terminal ends, dimethylsiloxane in which trimethylsiloxy groups are present at the terminal ends, 3.3.3-trifloropropylmethylsiloxane-dimethylsiloxane copolymer perfluoroalkyl group containing polysiloxane, and others.

The quantity of said silicone oil with respect to silicone rubber powder must be 0.5–80 weight percent preferably 3.0–50 weight percent.

Examples of silicone rubbers which constitute said silicone rubber powder include, but are not limited to, rubber obtained by curing addition reaction-curable silicone rubber composition consisting principally of diorganopolysiloxane which contains hydrogen bonded to silicon, organopolysiloxane which contains a vinyl group bonded to silicon, and platinum catalyst; a rubber obtained by curing condensation-curable silicone rubber composition consisting principally of diorganopolysiloxane in which hydroxyl groups are present at both molecular chain terminals organopolysiloxane which contains hydrogen bonded to silicon, and organotin compound; a rubber obtained by curing condensation-curable silicone rubber composition consisting principally of diorganopolysiloxane in which hydroxyl groups are present at both molecular chain terminals, hydrolyzable organosilane, and organotin compound or titanic acid ester (concrete examples of condensing reactions include dehydration, dealcoholation, deoximation, deamination, deamidation, decarboxylation, deketonation, etc.), peroxide-curable organopolysiloxane elastomer consisting principally of vinyl group-containing organopolysiloxane and organoperoxide catalyst; and rubber obtained by curing high-energy ray-curable silicone rubber composition which can be cured by irradiating gamma-rays, ultraviolet rays, or electron beams.

Of the aforementioned examples, the rubber obtained by curing the addition reaction-curable silicone rubber is especially desirable for curing rate and curing homogeneity. The preferred addition reaction-curable organopolysiloxane composition comprises (A) an organopolysiloxane which contains at least two intramolecular low-molecular-weight alkenyl groups, (B) an organopolysiloxane which contains at least two intramolecular silicon bonded hydrogen atoms, and (C) a platinum compound catalyst.

In the aforementioned composition, component (A) is the main ingredient of said addition reaction-curable silicone rubber composition. The present composition is cured by addition-reacting component (A) and component (B) due to the catalytic effects of component (C). Component (A) should be comprised of at least two intramolecular silicon-bonded low- molecular-weight alkenyl groups. If the number of the low- molecular weight alkenyl groups is below 2, it is impossible to form a network structure. Thus, it is impossible to produce a desirable cured product. The alkenyl groups may be exemplified by a vinyl group, allyl group, and propenyl group. The low-molecular-weight alkenyl groups may be present anywhere on the molecule, but desirable results are obtained if said groups are at the terminal ends of the molecule. The molecular structure of component (A) may be linear, branched, cyclic, or network-like. Preferred results are obtained if component (A) is linear (with or without some branching). There are no special restrictions of the molecular weight of the present component. Thus, low- viscosity liquids and high-viscosity, green, rubber-like substances can be equally used. To produce rubbery elastic cured product, however, organopolysiloxane with a viscosity (at 25° C.) of 100 centistoke or above is desirable.

Examples of component (A) organopolysiloxanes include, but are not limited to, methylvinylsiloxane in which trimethylsiloxy groups are present at the terminal ends, methylsiloxane-dimethylsiloxane copolymer in which trimethylsiloxy groups are present at the terminal ends, dimethylpolysiloxane in which dimethylvinylsiloxy groups are present at the terminal ends, dimethylsiloxanemethyl-phenylsiloxane copolymer in which dimethylvinylsiloxy groups are present at the terminal ends, dimethylsiloxane-diphenylsiloxane-methylvinylsiloxane copolymer in which dimethylvinylsiloxy groups are present at the terminal ends, dimethylsiloxane methylvinylsiloxane copolymer in which trim ethylsiloxy groups are present at the terminal ends, dimethylsiloxane methylphenylsiloxane-methylvinylsiloxane copolymer in which trimethylsiloxy groups are present at the terminal ends, methyl-(3,3,3-trifluoropropyl)polysiloxane in which methylvinylsiloxy groups are present at the terminal ends, and dimethylsiloxane-methyl-(3,3,3-trifluoropropyl)siloxane copolymer in which dimethylvinylsiloxy groups are present at the terminal ends.

The aforementioned organopolysiloxane which contains at least two intramolecular silicon-bonded hydrogen atoms, which is used as component (B), functions as a crosslinking agent for component (A). At least two silicon bonded hydrogen atoms be present in a single molecule of said component (B) to obtain satisfactory effects as a crosslinking agent.

There are no special restrictions on the molecular structure of component (B). For example, linear, branched/linear, or cyclic compounds can be used There are no special restrictions on the molecular weight of component (B). but for miscibility with component (A). the viscosity at 25° C. should be 1–50,000 centistoke.

The quantity of component (B) should be selected so that the molar ratio of total silicon-bonded hydrogen atom content of component (B) with respect to total low-molecular-weight alkenyl group content of component (A) will be 1.5 to 2.0:1. If the aforementioned molar ratio is below 0.5:1, it is difficult to obtain satisfactory curing efficiency. If said ratio exceeds 20:1, on the other hand, hardness tends to increase to excess if the resulting cured product is heated.

Examples of component (B) organopolysiloxanes include but are not limited to, methylhydrodienepolysiloxane in which trimethylsiloxy groups are present at the terminal ends, dimethylsiloxane-methylhydrodienepolysiloxane copolymer in which trimethylsiloxy groups are present at the terminal ends, and dimethylsiloxane-methylhydrodienesiloxane cyclic copolymer.

Component (C) is a catalyst which induces an addition reaction between the silicon-bonded hydrogen atoms of component (B) and the alkenyl groups of component (A). Examples of applicable catalysts include, but are not limited to, chloroplatinic acid, a solution obtained by dissolving said acid in alcohol or ketone, a product obtained by aging said solution, chloroplatinic acid-olefin complex compound, chloroplatinic acid-alkenylsiloxane complex compound, chloroplatinic acid-diketone complex compound, platinum black, and catalyst obtained by supporting platinum on a carrier.

The quantity of the present component (as platinum metal) with respect to 1,000,000 parts by weight of the combined weights of components (A) and (B) should be 0.1–1,000 parts by weight, preferably 1–100 parts by weight.

Examples of other organic groups which can be bonded to silicone atoms of the aforementioned organopolysiloxanes which constitute the main ingredient of the aforementioned curable organopolysiloxane composition include alkyl groups such as methyl, ethyl, propyl, and butyl; substituted alkyl groups such as 2-phenylethyl, 2 phenylpropyl, 3,3,3-trifluoropropyl; aryl groups such as phenyl, toluyl, xylyl; substituted aryl groups such as phenylethyl; and substituted monovalent hydrocarbon groups containing epoxy groups, carboxylic acid ester groups, mercapto groups, and others. Various methods can be used to manufacture the silicone rubber powder of the present invention. All conceivable methods can be used in the present invention.

In one desirable process the silicone oil is mixed with the aforementioned silicone rubber composition. After the resulting silicone oil-containing silicone rubber composition has been put in water, said composition is mixed with water in the presence or absence of surfactant (e.g , nonionic surfactants, anionic surfactants, cationic surfactants, and amphoteric surfactants). After the contents have been homogeneously mixed using an appropriate mixing mechanism such as a colloid mill or homomixer an aqueous dispersion of silicone oil-containing silicone rubber composition is obtained.

Subsequently, the resulting aqueous dispersion is put in hot water at 50° C. or below. Then it is cured and dried. In an alternative process, the aforementioned silicone oil- containing silicone rubber composition or aqueous dispersion containing said silicone oil-containing silicone rubber composition is directly atomized and cured in a hot stream. In still another process, silicone oil is mixed with high- energy-beam-curable silicone rubber composition. Then the resulting mixture is atomized and cured while high-energy beams are irradiated. In still another process, the aforementioned silicone rubber composition is cured by an ordinary method Then, t he resulting cured product is pulverized using a conventional pulverizing mechanism such as a ball mill, atomizer, kneader, or roll mill, to produce powder In the present invention, a powder derived from the aforementioned addition reaction-curable silicone rubber composition is especially desirable since fine and spherical powder with uniform particle size can be obtained The optimum concentration of the silicone rubber powder containing the silicone oil depends on the application and type of cosmetic composition into which it is being added. In general, there are no special restrictions. For solid or pasty cosmetic compositions, the concentration of the silicone rubber powder containing the silicone oil should be 0.5–50 percent by weight of the cosmetic composition. For creamy or emulsified cosmetic compositions, the concentration of the silicone rubber powder containing the silicone oil should be 0.1–30 percent by weight of the cosmetic composition.

When the cosmetic composition of the present invention is manufactured, the aforementioned silicone rubber powder containing the silicone oil and ordinary cosmetic composition ingredients are homogeneously mixed and dispersed.

Examples of said cosmetic composition ingredients include surfactants, oiling agents, fatty acids, alkaline substances, alcohols, esters, humidistat agents, tackifiers, pigments, dyes, purified water, and others. These ingredients may be used either lone or in combinations of two or more.

Examples of surfactants include nonionic surfactants such as sorbitan fatty acid esters, glycerin fatty acid ester, decaglycerin fatty acid esters, polyglycerin fatty acid esters, propylene glycol-pentaerythrito fatty acid esters, polyoxyethylene sorbitan fatty acid esters, polyoxyethylene sorbit fatty acid esters, polyoxyethylene glycerin fatty acid esters, polyethylene glycol fatty acid esters, polyoxyethylene alkyl ethers, polyoxyethylene phytosterol, phytostal, polyoxyethylene polyoxypropylene ether, polyoxyethylene alkyl ether, polyoxyethylene castor oil-cured castor oil, polyoxyethylenelanolin-lanolin alcohol- beeswax derivative, polyoxyethylenealkylamine-fatty acid amide, polyoxytetramethylene glyceryl alkyl ether, alkyl fatty acid triglyceride, and polyoxyalkylene-dimethylpolysiloxane copolymer; anionic surfactants such as alkylsulfates, polyoxyalkyl ether sulfates, N-acylaminates, alkylphosphates, polyoxyethylene alkylether phosphates and fatty acid salts; cationic surfactants such as alkylammonium salts, and alkylbenzylammonium salts; and amphoteric surfactants such as betaine acetate, imidazolium betaine, and lecithin.

Examples of oiling agents include vegetable oils such as linseed oil, soybean oil, castor oil, and coconut oil; animal oils such as egg yolk fat, mink oil, beef fat, pork fat, and squalane; mineral oils such as ceresin, paraffin, and microcrystalline wax; and silicone oils such as dimethyl-polysiloxane, methylphenylpolysiloxane, methylhydrodiene-polysiloxane, amino-modified polysiloxanes, cyclomethylpolysiloxanes, cyclomethylphenylpolysiloxanes, cyclomethylhydrodienepolysiloxanes, and epoxy-modified polysiloxanes.

Examples of fatty acids include myristic acid, lauric acid, palmitic acid, stearic acid, behenic acid, lanolic acid, isostearic acid, undecyleic acid, hydrogenated animal fatty acids, hydrogenated vegetable fatty acids, and triple-press fatty acids.

Examples of alkaline substances include sodium hydroxide, potassium hydroxide, calcium hydroxide, diethanolamine, triethanolamine, and others.

Examples of alcohols include low-molecular-weight alcohols such as ethanol, n-propyl alcohol, isopropyl alcohol, and butanol; and high-molecular-weight alcohols such as lauryl alcohol, cetanol, stearyl alcohol, oleyl alcohol, lanolin alcohol, hydrogenated lanolin alcohol, hexyldecanol, octyldodecanol, and behenyl alcohol.

Examples of esters include fatty acid esters such as isopropyl myristate, butyl stearate, octyldodecyl neodecanate, and cholesteryl stearate; and polyalcohol fatty acid esters such as propylene glycol didecanate, and glycerin tri-2-ethylhexanate.

Examples of humidistar agents include glycerin, propylene glycol, sorbitol, 1,3-butylene glycol, polyethylene glycol, urea, sodium lactate, sodium pyrrolidonecarboxylate, polypeptide, pyroallonic acid, acylamino acid, and others.

Examples of tackifiers include natural polymers such as guar gum, carageenan, alginic acid, gum arabia, traganth gum, pectin, starch, xanthan gum, gelatin, casein, and albumin; semisynthetic polymers such as locust bean gum derivatives, cellulose derivatives, and alginic acid derivatives; and synthetic polymers such as polyvinyl alcohol, polyvinylpyrrolidone, polyvinyl methacrylate, polysodium methacrylate, and polyethylene glycol.

The cosmetic composition of the present invention, furthermore, may additionally contain non-silicone powders as inferior components as long as they exert no adverse effects on the objectives of the present invention. Concrete examples of such nonsilicone powders include (pulverized) seeds such as apricot, almond, birch, walnut, peach, sunflower, and watermelon; vegetable powders such as cured jojoba oil, and cured coconut oil; animal powders Such as pulverized crab shell, and pulverized eggshell, cured beef fat, cured pork fat; organic resin powders such as polyethylene, nylon, polypropylene, polyvinyl chloride, polystyrene, and cellulose; and inorganic powders such as aluminum oxide, silica, talc, and zirconium oxide.

The cosmetic composition of the present invention can be easily manufactured by homogeneously mixing the cosmetic composition ingredients and the silicone rubber powder using methods known in the art.

So that those skilled in the art can understand and appreciate the invention taught herein the following examples are presented, it being understood that these examples should not be used to limit the scope of this invention over the limitations found in the claims attached hereto.

In the subsequent Application Examples and Reference Examples, "parts" and "Me" mean "parts by weight" and "methyl group", respectively.

REFERENCE EXAMPLE 1

Preparation of Organopolysiloxane Elastomer:

100 parts of dimethylpolysiloxane represented by the following formula:

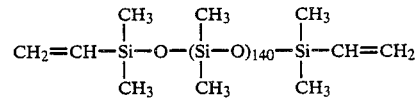

in which dimethylvinylsiloxy groups were present at the terminal ends, 4.7 parts of partially branched linear methylhydrodienepolysiloxane with the following average compositional formula: $(Me)_{15}(H)_7(SiO)_9$, 50 parts of dimethyl silicone oil (viscosity at 25° C.: 100 cst). 2.5 parts of polyoxyethylene alkyl ether-type nonionic Surfactant (Targitol TMN-6, manufactured by Union Carbide Co.), 100 parts of water and isopropanol solution containing chloroplatinic acid (concentration as platinum metal with respect to total organopolysiloxane weight: 100 ppm) were mixed. After the resulting mixture had subsequently been put in a colloid mill, an aqueous silicone rubber composition dispersion was obtained. The resulting aqueous dispersion was added dropwise to a hot water bath at 60° C. to cure the aforementioned silicone rubber composition. Thus, a silicone oil-containing silicone rubber powder was obtained When the resulting silicone oil-containing silicone rubber powder was analyzed using a scanning electron microscope, it was determined that said powder consisted of spherical particles with an average particle size of 7.5 μm. It was also determined that said powder had excellent rubbery elasticity. When the dimethyl silicone oil content of 100 g of the silicone rubber powder was Soxhlet-extracted (extracting solvent: acetone), 35 g of the dimethyl silicone oil was extracted.

COMPARATIVE EXAMPLE 1

A silicone oil-free silicone rubber powder consisting of spherical particles (average particle size: 7.5 μm) was prepared according to identical procedures except that no dimethyl silicone oil was used.

APPLICATION EXAMPLE 1

Oily Foundation

After 4 parts of microcrystalline wax, 4 parts of ozokerite 2.0 parts of lanolin alcohol, 3 parts of fluid paraffin, 1 part of sorbitan sequioleate, 35 parts of decamethylcyclopentasiloxane, and 2 parts of isopropyl myristate had been put in a container with an agitation mechanism, the contents were heated and melted at 70–80° C. After 15 parts of titanium dioxide, 20 parts of kaolin, 5 parts of talc, 3 parts of red oxide, and 6 parts of silicone oil-containing silicone rubber powder obtained in Reference Example 1 had been added to the resulting mixture, the contents were homogeneously mixed. After the resulting mixture had been cooled and degassed, a small quantity of perfume was added to and mixed with the resulting mixture. Thus, an oily foundation was obtained. The resulting oily foundation was coated on the inner and upper left arm of five panelists in order to evaluate coating texture and coating state. The results are summarized in Tables I and II.

For comparison, an oily foundation was prepared according to identical procedures except that the silicone oil-free silicone rubber powder obtained in Comparative Example 1 was used in place of the silicone oil-containing silicone rubber. The evaluation results on this foundation are also summarized in Tables I and II.

TABLE I

| Panelist/Categories | Present Invention | Comparative Example |
|---|---|---|
| Panelist 1 | Dry texture | Somewhat grainy texture |
| Panelist 2 | Fading sensation | Squeaky texture |
| Panelist 3 | Dry texture | Squeaky texture |
| Panelist 4 | Dry texture | Slightly grainy texture |
| Panelist 5 | Dry texture | No foreign sensation |

TABLE II

| Panelist/Categories | Present Invention | Comparative Example |
|---|---|---|
| Panelist 1 | Homogeneous surface state | Uneven color |
| Panelist 2 | Homogeneous surface state | No uneven color but flocculate present |
| Panelist 3 | Homogeneous surface state | Uneven color and flocculate present |
| Panelist 4 | Homogeneous surface state | No uneven color but a small guantity of flocculate present |
| Panelist 5 | Homogeneous surface state | Homogeneous surface state |

APPLICATION EXAMPLE 2

Lipstick

After 12 parts of paraffin wax, 12 parts of lanolin alcohol. 10 parts of kaolin, 40 parts of sunflower oil, 10 parts of dimethylpolysiloxane (viscosity: 1 cst), 2.5 parts of glycerin trioctanate, 3 parts of candelilla wax, 6.0 parts of the silicone oil-containing silicone rubber powder obtained in Reference Example 1, 1.0 part of titanium oxide, 1.0 part of red No. 201, 2.0 parts of red No. 202, and 0.5 part of aluminum lake blue No. 1 had been fed, the contents were heated, melted, and homogeneously mixed. After the resulting mixture had been homogeneously redissolved using a roll mill, a small quantity of perfume was added. Then, the contents were homogeneously mixed. After the resulting mixture had been degassed it Was poured into a metal lipstick mold. After said mixture had been rapidly cooled, a lipstick was obtained.

The resulting lipstick was coated on the inner and upper left arm of five panelists to evaluate coating texture and coating state. The results are summarized in Tables III and IV.

For comparison, a lipstick was prepared according to identical procedures except that the silicone oil-free silicone rubber powder obtained in Comparative Example 1 was used in place of the silicone oil-containing silicone rubber. The resulting lipstick was coated on the inner and upper left arm of five panelists to evaluate coating texture and coating state. The evaluation results on this foundation are also summarized in Tables III and IV.

TABLE III

| Panelist/Categories | Present Invention | Comparative Example |
|---|---|---|
| Panelist 1 | Moist texture | Somewhat grainy texture |
| Panelist 2 | Moist texture | Slightly grainy texture |
| Panelist 3 | Dry texture | Fracture during coating |
| Panelist 4 | Moist texture | Slightly grainy texture |
| Panelist 5 | Dry texture | No foreign sensation |

TABLE IV

| Panelist/Categories | Present Invention | Comparative Example |
|---|---|---|
| Panelist 1 | Homogeneous surface texture | Color streaks present |
| Panelist 2 | Homogeneous surface texture | No color streaks but flocculate present |
| Panelist 3 | Homogeneous surface texture | Color streaks and flocculate present |
| Panelist 4 | Homogeneous surface texture | No uneven color |
| Panelist 5 | Homogeneous surface texture | Homogeneous surface texture |

APPLICATION EXAMpLE 3

Moisturizing cream 9.0 parts of microcrystalline wax, 2.0 parts of solid paraffin 3.0 parts of beeswax, 5.0 parts of Vaseline, 3 0 parts of the silicone oil-containing silicone rubber powder obtained in Reference Example 1, 8 parts of reduced lanolin, 15 parts of fluid paraffin, 12 parts of squalane, 4 parts of isopropyl myristate, 8 parts of hexadecyladipic acid ester, 2 parts of dimethylpolysiloxane (viscosity at 25° C. 350 cst), and 3 parts of lipophilic glycerin monooleate were heated, melted, and mixed at 70° C. The resulting mixture was mixed with a mixture consisting of 1.0 part of polyoxyethylene (21) lauryl ether, 2.0 parts of glycerin, and a balance of purified water, which was being heated at 70° C. The resulting mixture was cooled to 30° C. or below. The moisturizing cream mixture was put into a container. The resulting moisturizing cream was coated on the inner and upper left arm of five panelists to evaluate coating texture and coating stare. The results are summarized in Tables V and VI.

For comparison, a moisturizing cream was prepared according to identical procedures except that the silicone oil-free silicone rubber powder obtained in Comparative Example 1 was used in place of the silicone oil-containing silicone rubber. The resulting moisturizing cream was coated on the inner and upper left arm of five panelists to evaluate coating texture and coating state. The evaluation results on this foundation are also summarized in Tables V and VI.

TABLE V

| Panelist/Categories | Present Invention | Comparative Example |
|---|---|---|
| Panelist 1 | Moist texture | Somewhat grainy texture |
| Panelist 2 | Moist texture | Slightly grainy texture |
| Panelist 3 | Dry texture | Some grainy texture |
| Panelist 4 | Moist texture | Slightly grainy texture |
| Panelist 5 | Dry texture | No foriegn sensation |

TABLE VI

| Panelist/Categories | Present Invention | Comparative Example |
|---|---|---|
| Panelist 1 | Homogeneous surface texture | Secondary flocculate present |
| Panelist 2 | Homogeneous surface texture | Flocculate present |
| Panelist 3 | Homogeneous surface texture | Flocculate present |
| Panelist 4 | Homogeneous surface texture | Homogeneous surface texture |
| Panelist 5 | Homogeneous surface texture | Homogeneous surface texture |

What is claimed is:

1. A cosmetic composition comprised of
   (I) a silicone rubber powder containing 0.5–80 wt% of silicon oil wherein the silicone oil is incorporated into the silicone rubber powder prior to the cure of the silicone rubber powder; and
   (II) at least one cosmetic ingredient selected from surfactants, oiling agents, fatty acids, alkaline substances, alcohols, esters, humidistat agents, tackifiers, pigments, dyes, and purified water.

2. The cosmetic composition specified in claim 1 in which the viscosity of said silicone oil at 25° C. is 1000 centistoke.

3. The cosmetic composition specified in claim 1 in which the silicone rubber powder content is 0.5–50 percent by weight.

* * * * *